US006984392B2

(12) United States Patent
Bechert et al.

(10) Patent No.: US 6,984,392 B2
(45) Date of Patent: Jan. 10, 2006

(54) ANTIMICROBIAL MATERIAL FOR IMPLANTING IN BONES

(75) Inventors: Thorsten Bechert, Hallstadt (DE); Peter Steinrücke, Erlangen (DE)

(73) Assignee: Bio-Gate Bioinnovative Materials GmbH, Nuremberg (DE)

( * ) Notice: Subject to any disclaimer, the term of this patent is extended or adjusted under 35 U.S.C. 154(b) by 43 days.

(21) Appl. No.: 10/363,120

(22) PCT Filed: Aug. 28, 2001

(86) PCT No.: PCT/DE01/03210

§ 371 (c)(1),
(2), (4) Date: Apr. 28, 2003

(87) PCT Pub. No.: WO02/17984

PCT Pub. Date: Mar. 7, 2002

(65) Prior Publication Data
US 2003/0165556 A1 Sep. 4, 2003

(30) Foreign Application Priority Data
Aug. 31, 2000 (DE) ................................. 100 43 151

(51) Int. Cl.
*A61F 13/00* (2006.01)
*A61F 2/00* (2006.01)

(52) U.S. Cl. ...................................... 424/422; 424/423

(58) Field of Classification Search ................. 424/422
See application file for complete search history.

(56) References Cited

U.S. PATENT DOCUMENTS

| 4,592,920 A |   | 6/1986  | Murtfeldt ...................... 427/2 |
| 4,849,223 A | * | 7/1989  | Pratt et al. .................. 424/409 |
| 5,171,579 A | * | 12/1992 | Ron et al. .................... 424/486 |
| 5,356,629 A | * | 10/1994 | Sander et al. ............... 424/422 |
| 5,590,387 A |   | 12/1996 | Schmidt et al. ............... 419/36 |
| 5,595,750 A | * | 1/1997  | Jacobson et al. ........... 424/421 |
| 5,814,272 A |   | 9/1998  | Zeller et al. ................ 264/653 |
| 5,837,275 A |   | 11/1998 | Burrell et al. .............. 424/409 |
| 5,895,419 A |   | 4/1999  | Tweden et al. ................. 623/2 |
| 6,123,731 A | * | 9/2000  | Boyce et al. ............. 623/23.63 |

FOREIGN PATENT DOCUMENTS

| DE | 32 28 849 A1 |   | 2/1984 |
| EP | 0 650 945 A2 |   | 5/1995 |
| WO | WO 82/01990  | * | 6/1982 |
| WO | WO 84/01721  |   | 5/1984 |
| WO | WO/95/18637  |   | 7/1995 |
| WO | WO/99/26666  |   | 6/1999 |

* cited by examiner

*Primary Examiner*—Thurman K. Page
*Assistant Examiner*—Retford Berko
(74) *Attorney, Agent, or Firm*—Pearne & Gordon LLP

(57) ABSTRACT

The invention relates to an antimicrobial material for implanting in bones and for coating or producing an implant or an implantable medical device, whereby particles formed from an antimicrobial material are remotely dispersed inside a matrix material that forms a matrix when hardened. In order to improve the compatibility of the antimicrobial material, the invention provides that the metal is formed from aggregates of primary particles having an average particle size ranging from 10 to 100 nm.

34 Claims, 2 Drawing Sheets

ANTIMICROBIAL MATERIAL FOR IMPLANTING IN BONES

CROSS-REFERENCE TO RELATED APPLICATIONS

This application is a National Stage application under 35 U.S.C. §371 and claims benefit under 35 U.S.C. §119(a) of International Application No. PCT/DE/0103210 having an International Filing Date of Aug. 28, 2001, which claims benefit of DE 100 43 151.8 filed on Aug. 31, 2000.

The invention relates to an antimicrobial material for implanting in bones, for coating or producing implants or an implantable device corresponding to the preamble of claim 1. It further relates to a process for producing such a material.

EP 0 190 504 discloses an antimicrobial composition which contains 5 to 10% by weight of silver. In addition, to improve the antimicrobial properties, a hydratable or a hydrated oxide is added.

DE 31 10 681 C2 describes a material for bone implants. The material is produced from a polymer to which silver phosphate is added as antimicrobial agent.

WO 81/02667 discloses an antimicrobial surgical implant. Metallic silver is added to the implant as antimicrobial agent.

The generic WO 82/01990 describes a bone cement based on polymethylmethacrylate as main component, to which 5% by volume of a silver salt is added as antimicrobial agent.

U.S. Pat. No. 5,837,275 discloses an antimicrobial material which contains, inter alia, silver particles with a particle size of less than 200 nm. The silver lattice has lattice disorders and defects in order to facilitate release of silver ions.

WO 84/01721 discloses a material provided with silver sulfate or silver azetate. This material releases a concentration of more than $1\mu M$ silver ions in a surrounding fluid within 24 hours.

DE 32 288 849 A1 describes a material with a coating made of silver. Elemental carbon or titanium is added to the material. The addition is intended to facilitate increased release of silver ions into the surroundings.

U.S. Pat. No. 4,849,233 discloses a bone cement to which about 10% by weight of elemental silver plus titanium oxide or tantalum oxide are added. The bone cement is distinguished by a high rate of release of silver ions.

The antimicrobial activity of the materials disclosed in the prior art has been detected using the so-called measurement of zones of inhibition. Measurement of zones of inhibition is described, for example, in Raad I. et al., J. Infec. Dis. 173 (1996). This entails the material to be tested being embedded in a nutrient medium, e.g. agar. A zone of inhibition forms around the material because of the release of metal ions with antimicrobial activity. The formation and the size of such a zone of inhibition has been regarded in the prior art as indicating the antimicrobial activity of the material. The materials known in the prior art have in some cases the disadvantage that they release a sufficiently high concentration of silver ions for only a relatively short time. Their antimicrobial activity is restricted to this time. In order to counteract this disadvantage, relatively large amounts of metals with antimicrobial activity are added in the prior art. This in turn leads to unwanted cytotoxic effects in vivo.

It is an object of the invention to eliminate the disadvantages of the prior art. It is intended in particular to indicate an antimicrobial material which has improved properties and which can be produced as easily and inexpensively as possible. The tolerability of the material by the patient should be maximal. It is additionally intended to indicate a process for producing the antimicrobial material.

This object is achieved by the features of claims 1 and 14. Expedient embodiments are evident from the features of claims 2 to 13 and 15 to 27.

The invention provides for the metal to be formed from aggregates of primary particles having an average particle size between 10 and 100 nm.

The primary particles in the aggregates of the invention can still be identified on the basis of their external shape. The primary particles are bound together essentially by necks formed during sintering. The aggregates form a highly porous framework structure. The matrix material may, depending on the particular embodiment, be essentially bioinert.

The proposed material is distinguished by an excellent antimicrobial activity. A sufficiently high concentration of silver ions is made available on the surface of the material. Moreover the rate of diffusion of silver ions into the surrounding tissue is particularly low. This means that the antimicrobial activity remains confined to the surface of the material. It is possible with the material of the invention to produce, for example, bone cements, implants or else implantable devices such as catheters, with improved antimicrobial properties. No unwanted cytotoxic effects occur. The antimicrobial effect of the material is particularly long-lasting. The pharmacological stress on the patient is less.

In an advantageous embodiment, the aggregates have an average particle size of from 1 to 20 $\mu$m, preferably 10 to 20 $\mu$m. The surface area of the aggregates is expediently from 3 to 6 $m^2/g$. They may have a porosity of up to 95%. The porosity is expediently between 70 and 95%. The aforementioned features contribute to a uniform and cytotoxically unobjectionable delivery of silver ions on the surface of the material.

The aggregates can be produced by inert gas vaporization and condensation, preferably under a pressure of from 10 to 100 mbar of inert gas. The metal may be formed from one or more of the following components: Ag, Au, Pt, Pd, Ir, Sn, Cu, Sb, Zn. The metal expediently has an essentially undisordered lattice structure. This avoids undesirably high release of silver ions into the surrounding tissue.

According to a particularly advantageous embodiment feature, the metal content is not more than 2% by weight, preferably 0.01 to 2% by weight, based on the weight of the matrix material. Silver is expediently used as metal. The proposed addition of metal is relatively small. The material can be produced inexpensively.

It has further proved to be expedient for the aggregates to be completely infiltrated with the matrix material. It is advantageous for the aggregates to be homogeneously dispersed or distributed in the matrix material. These features contribute to the amount of silver ions released always being the same at all sites on the surface of the material.

The matrix material may be a polymer preferably formed from a plurality of components. The polymer may essentially comprise acrylic esters and/or methacrylic esters. However, other matrix materials used in the prior art for producing bone cements are also suitable as matrix material.

The proposed antimicrobial material is suitable for producing or else for coating implants or an implantable medical device, e.g. a catheter or intratracheal tubes. It is possible in particular to use the proposed antimicrobial material to coat or produce hip joint implants, heart valves, stents, knee joint implants, dental fillings, contact lenses or intraocular lenses, produced, for example, from titanium or ceramic.

In addition, a process for producing the material according to the invention is proposed, having the following steps:

a) vaporization and condensation of metal under inert gas atmosphere, where the pressure of the inert gas and the vaporization temperature are adjusted so that aggregates consisting of primary particles having an average particle size of from 10 to 100 nm are formed, and b) mixing of the aggregates with a curable matrix material.

The proposed process is relatively easy to carry out. It is possible thereby to produce the antimicrobial material in uniform quality and relatively inexpensively.

According to one embodiment feature, the aggregates are classified after step a). It is expedient for a particle size fraction of the aggregates in the range from 1 to 20 μm, preferably 10 to 20 μm, to be mixed with the matrix material, which is preferably in the liquid state. The particle size fraction can be stirred into the matrix material.

It has proved to be expedient to use an inert gas which comprises as an essential component at least one of the following gases: argon, krypton, xenon, helium.

Reference is made to the preceding statements concerning further advantageous embodiments. The features described there can also be applied analogously in the process.

Exemplary embodiments of the invention are described in detail below with reference to the drawing. These show FIG. 1 bacterial proliferation on bone cements, comparing silver powders of the prior art and the silver powder of the invention, FIG. 2 a scanning electron micrograph of a silver aggregate, FIG. 3 the dependence of the cytotoxicity of a bone cement as a function of the silver content and FIG. 4 a zone of inhibition test for various bone cements.

The results shown in FIG. 1 were obtained by the method disclosed in DE 197 51 581 A1. This method is further described in Bechert, Throsten et al., Nature Medicine, Vol. 6, No. 8 (September 2000). The disclosure of both the aforementioned documents is incorporated herein by reference.

Initially in each case 8 parallel samples (A–H) are made from the same batch of bone cement. The samples are normally cylindrical in shape. They have a length of about 1 cm and a diameter of from 2 to 5 mm. Subsequently, 200 μl of a bacteria-containing solution are introduced into each well of a microtiter plate. The samples are incubated at 37° C. for one hour. The samples are then removed and washed three times with physiological buffers. The samples are then placed in the wells of a microtiter plate which are filled with a minimal medium. 200 μl of minimal medium are introduced into each well. The samples are incubated at 37° C. for 24 hours. The samples are then removed and discarded. 50 μl of a complete medium (trypticase soya) are added to each well of the microtiter plate. The turbidity of the solution is then measured at 30-minute intervals over a period of 48 hours. The solution is kept at a temperature of 37° C. during this. The turbidity is measured by means of a suitable reader using light of a wavelength of 578 nm. A turbidity indicates that bacteria have been released from the surface of the sample into the surroundings.

FIG. 1 shows a comparison of a bone cement to which various contents of conventional silver powder supplied by Chempur (columns 2–6) have been added with a second bone cement to which comparable amounts of silver aggregates of the invention have been added (columns 7 to 11).

2.0% by weight of silver have been added to the samples of columns 2 and 7, 1.0% by weight of silver to the samples of columns 3 and 8, 0.5% by weight of silver to the samples of columns 4 and 9, 0.1% by weight of silver to the samples of columns 5 and 10 and 0.05% by weight of silver to the samples of columns 6 and 11. Column 12 shows the results of samples without added silver (control).

It is evident that addition of only 1.0% by weight of silver aggregates of the invention results in an excellent antimicrobial activity. When conventional silver powders are used, no reliable antimicrobial activity is achieved even on addition of 2.0% by weight.

FIG. 2 shows a scanning electron micrograph of the silver aggregate of the invention. The silver aggregate consists essentially of spherical primary particles with an average particle size of about 20 nm. The primary particles are essentially connected together by necks formed during sintering. They form a highly porous structure. The silver aggregate shown here has a size of about 10 μm.

FIG. 3 shows the results of the cytotoxic effect of the bone cements of the invention. The method used here was the test of Greil et al. (Infection, Vol. 27, 1999, Suppl. 1, pp. 34–37). This entails a tetrazole dye (MTT) being converted into an intensely colored formazan by a vital cell line showing respiratory activity (MRC-5 cells or by phytohemagglutinin-stimulated lymphocytes). The extent of the coloration achieved in a predefined time period is a measure of the vitality of the cells. The test is carried out in accordance with the ISO guideline. For this purpose, initially samples are incubated extracts of the bone cement with culture medium at 37° C. for 24 hours. The samples are incubated in the formazan assay together with the cells for a period of 72 hours. The cytotoxicity is defined as the relative percentage loss of respiratory activity through formazan formation as a consequence of addition of the extract.

Extracts obtained in accordance with the ISO guideline from PVC in independent experiments served as positive control. Cytotoxicity levels of greater than or equal to 30% are regarded as cytotoxic effects. The controls used were extracts of PE (negative control) and PVC (positive control).

Figure 2:
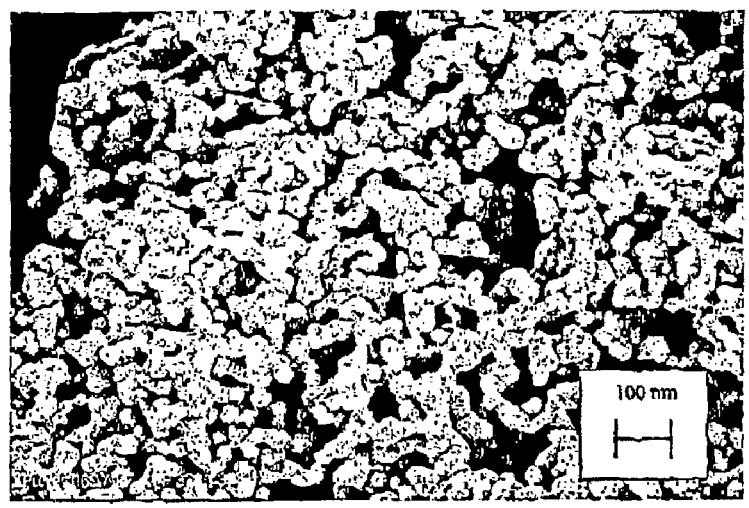
Figure 1:
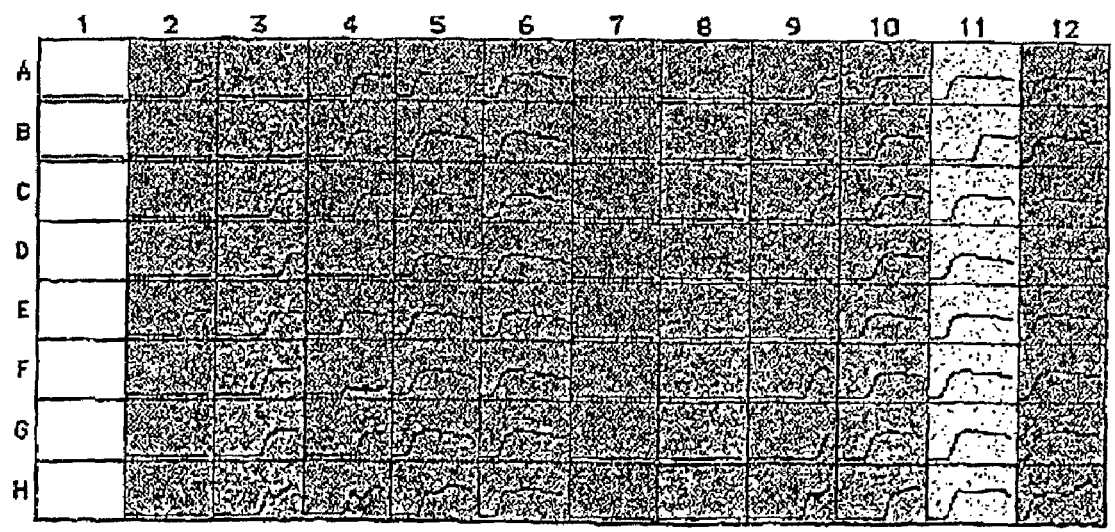
Figure 3:
FIG. 3a shows the result of an extract diluted 1:10 for positive control with lymphocytes. The cytotoxicity in this case is 100%.
FIG. 3b shows the result of the positive control with MRC-5 cells. The cytotoxicity in this case is 60%.
FIG. 3c shows the result using a bone cement of the invention with addition of 1.0% by weight of silver aggregate. The cytotoxicity in this case was only 8.4% for lymphocytes and 4.8% for MRC-5 cells (FIG. 3d).
Figure 4:
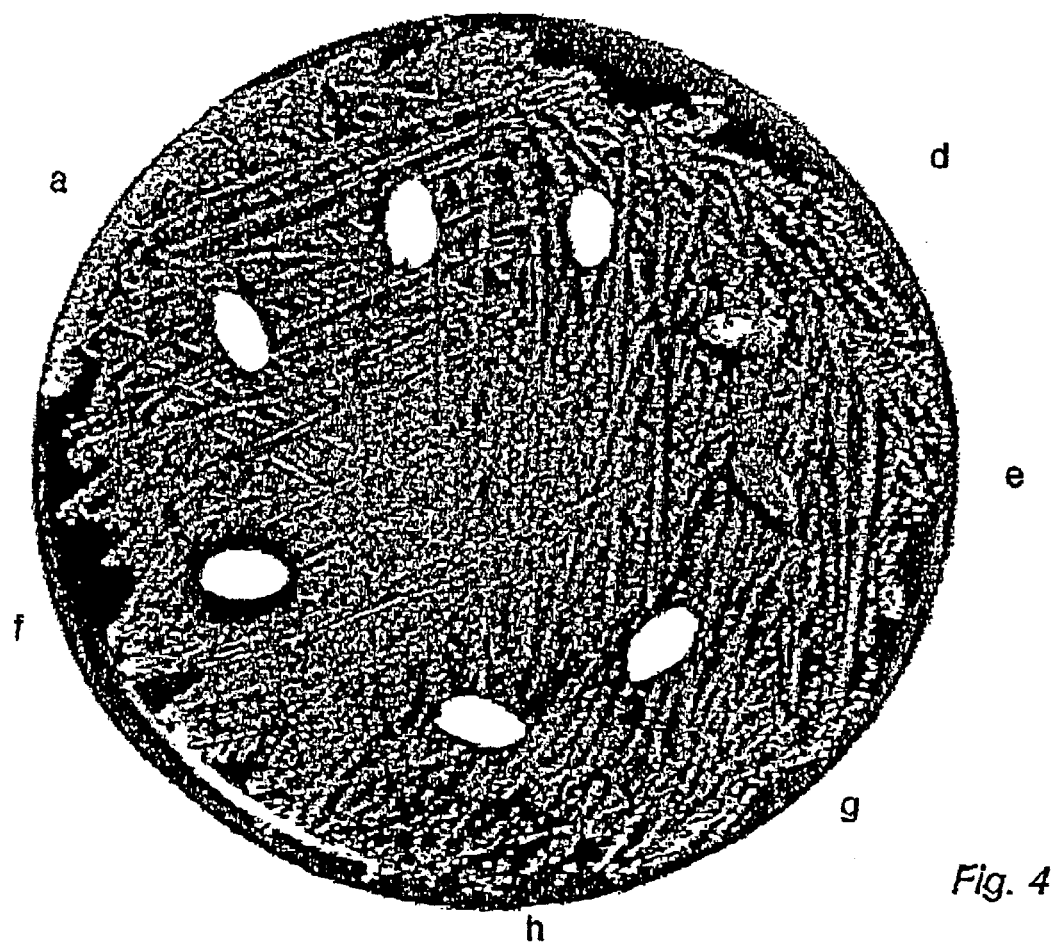
FIG. 4 shows the results of a measurement of the zone of inhibition with bone cements of the invention compared with conventional bone cements. The sample composition was as follows.

| | |
|---|---|
| sample a: | bone cement with 0.05% by weight of silver aggregates, |
| sample b: | bone cement with 0.1% by weight of silver aggregates, |
| sample c: | bone cement with 0.5% by weight of silver aggregates, |
| sample d: | bone cement with 2.0% by weight of silver aggregates, |
| sample e: | bone cement with 5.0% by weight of silver aggregates, |
| sample f: | conventional gentamycin-containing bone cement (Merck "Palacos") |

-continued

| sample g, h: | conventional bone cements without additions (Merck "Palacos") |

Samples a to h had, in order to carry out the measurement of the zones of inhibition, been embedded in a Müller-Hinton agar which had been incubated with coagulase-negative staphylococci as test microbe for 24 hours. No zone of inhibition is evident with the bone cements containing silver aggregates. By contrast, the conventional gentamycin-containing bone cement shows a clear zone of inhibition. The bone cements of the invention thus release only a small concentration of silver ions into the surroundings.

What is claimed is:

1. An antimicrobial implant material for implanting in bones, the material comprising:
   aggregates formed from an anti-microbial metal; and
   a polymer matrix material which forms a matrix in the cured state,
   wherein the aggregates are discrete and finely dispersed in said matrix material, wherein the aggregates are highly porous and are formed of primary particles connected together by necks, wherein the primary particles have an average particle size between 10 and 100 nm, and wherein the metal is not more than 5.0% by weight based on the weight of the polymer matrix material.

2. The antimicrobial material of claim 1, wherein the aggregates have an average aggregate size of from 1 to 20 μm.

3. The antimicrobial material of claim 2, wherein the aggregates have an average aggregate size of 10 to 20 μm.

4. The antimicrobial material of claim 1, wherein the aggregates have a surface area of from 3 to 6 $m^2$ per gram.

5. The antimicrobial material of claim 1, wherein the aggregates have a porosity of up to 95%.

6. The antimicrobial material of claim 1, wherein the aggregates are produced by inert gas vaporization and condensation.

7. The antimicrobial material of claim 6, wherein the aggregates are produced under a pressure of from 10 to 100 mbar of inert gas.

8. The antimicrobial material of claim 1, wherein the metal is formed from one or more of the following components: Ag, Au, Pt, Pd, Ir, Sn, Cu, Sb, Zn.

9. The antimicrobial material of claim 1, wherein the metal has an essentially undisordered lattice structure.

10. The antimicrobial material of claim 1, wherein the metal content is not more than 2.0% by weight based on the weight of the polymer matrix material.

11. The antimicrobial material of claim 10, wherein the metal content is 0.01 to 2.0% by weight, based on the weight of the polymer matrix material.

12. The antimicrobial material of claim 1, wherein the aggregates are completely infiltrated with the polymer matrix material.

13. The antimicrobial material of claim 1, wherein the polymer matrix material is formed from a plurality of components.

14. The antimicrobial material of claim 1, wherein the polymer matrix material comprises acylic esters and/or methacrylic esters.

15. The antimicrobial material of claim 1, wherein the aggregates are homogeneously dispersed in the polymer matrix material.

16. An implant or implantable medical device formed from, or at least partially coated with, the antimicrobial implant material of claim 1.

17. A process for producing the antimicrobial material of claim 1, comprising the steps of:
   a) vaporizing and condensing the metal under an inert gas atmosphere, wherein the pressure of the inert gas and the vaporization temperature are adjusted so that discrete aggregates consisting of primary particles having an average particle size of from 10 to 100 nm are formed, and
   b) mixing the aggregates with a curable polymer matrix material.

18. The process of claim 17, wherein the aggregates are size classified after step (a).

19. The process of claim 17, wherein the aggregates are sized classified to have an average aggregate size in the range of from 1 to 20 μm.

20. The process of claim 17, wherein the aggregates are size classified to have an average aggregate size in the range of 10 to 20 μm.

21. The process of claim 19, wherein the polymer matrix material is in the liquid state.

22. The process of claim 17, wherein the inert gas comprises at least one of the following gases: argon, krypton, xenon, helium.

23. The process of claim 17, wherein the aggregates have a surface area of from 3 to 6 $m^2$ per gram.

24. The process of claim 17, wherein the aggregates have a porosity of up to 95%.

25. The process of claim 17, wherein the metal is formed from one or more of the following constituents: Ag, Au, Pt, Pd, Ir, Sn, Cu, Sb, Zn.

26. The process of claim 17, wherein the metal has an essentially undisordered lattice structure.

27. The process of claim 17, wherein the matrix comprises not more than 2.0% of metal based on the weight of the polymer matrix material.

28. The process of claim 27, wherein the matrix comprises 0.01 to 2.0% of metal based on the weight of the polymer matrix material.

29. The process of claim 17, wherein the aggregates are completely infiltrated with the polymer matrix material.

30. The process of claim 17, wherein the polymer matrix material is formed from two component.

31. The process of claim 17, wherein the polymer matrix material comprises acylic esters and/or methacrylic esters.

32. The process of claim 17, wherein the aggregates are homogeneously dispersed in the polymer matrix material.

33. The process of claim 30, wherein the aggregates are initially admixed with one of the two polymer components.

34. An antimicrobial implant material for coating or producing an implant or an implantable medical device, comprising discrete aggregates formed from anti-microbial metal dispersed in a polymer matrix material which forms a matrix in the cured state, wherein the aggregates are highly porous aggregates formed of primary particles connected together by necks, wherein the primary particles have an average particle size between 10 and 100 nm, and wherein the metal content is not more than 5.0% by weight based on the weight of the polymer matrix material.

* * * * *